(12) United States Patent
Takeuchi et al.

(10) Patent No.: US 11,213,191 B2
(45) Date of Patent: Jan. 4, 2022

(54) OPTICAL FIBER ARRANGEMENT FOR ENDOSCOPE

(71) Applicant: CANON U.S.A., INC., Melville, NY (US)

(72) Inventors: Seiji Takeuchi, Newton, MA (US); Mitsuhiro Ikuta, Cambridge, MA (US); Anderson Thi Mach, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 386 days.

(21) Appl. No.: 16/248,607

(22) Filed: Jan. 15, 2019

(65) Prior Publication Data

US 2019/0223706 A1 Jul. 25, 2019

Related U.S. Application Data

(60) Provisional application No. 62/621,945, filed on Jan. 25, 2018.

(51) Int. Cl.
*A61B 1/00* (2006.01)
*A61B 1/05* (2006.01)
(Continued)

(52) U.S. Cl.
CPC ............ *A61B 1/05* (2013.01); *A61B 1/00096* (2013.01); *A61B 1/00167* (2013.01);
(Continued)

(58) Field of Classification Search
None
See application file for complete search history.

(56) References Cited

U.S. PATENT DOCUMENTS 3,776,222 A * 12/1973 Smiddy ................ A61B 1/0056
600/146
4,736,734 A 4/1988 Matsuura et al.
(Continued)

FOREIGN PATENT DOCUMENTS

JP 05-027120 A 2/1993
JP 2005-118429 A 5/2005
(Continued)

OTHER PUBLICATIONS

English Translation of JPH 0527120, originally published in 1993, translation from Aug. 17, 2021. (Year: 2021).*

(Continued)

*Primary Examiner* — Timothy J Neal
(74) *Attorney, Agent, or Firm* — Canon U.S.A., Inc., IP Division

(57) ABSTRACT

An endoscopic probe extending from a proximal end to a distal end thereof, and configured to be inserted in a tubular lumen to observe a sample is disclosed. The probe includes a first waveguide enclosed within an inner sheath and extending from the proximal end to the distal end along an axis of the inner sheath; and a plurality of second waveguides having at least the distal ends thereof arranged in one or more rings around the inner sheath to surround the distal end of the first waveguide. At the distal end, the axis of each of the second waveguides is tilted with respect to the axis of the first waveguide by a tilt angle which can be adjustable. This novel endoscopic probe has a resultant numerical aperture larger than the numerical aperture of each of the second waveguides, and it may be applicable to forward-viewing spectrally encoded endoscopes (SEE).

19 Claims, 10 Drawing Sheets

(51) Int. Cl.
- *A61B 1/06* (2006.01)
- *G02B 6/10* (2006.01)
- *A61B 1/07* (2006.01)
- *G02B 23/24* (2006.01)
- *F21V 8/00* (2006.01)
- *G02B 6/44* (2006.01)
- *G02B 6/42* (2006.01)
- *G02B 6/36* (2006.01)

(52) U.S. Cl.
CPC .............. *A61B 1/0607* (2013.01); *A61B 1/07* (2013.01); *G02B 6/10* (2013.01); *G02B 23/2446* (2013.01); *G02B 6/0008* (2013.01); *G02B 6/3604* (2013.01); *G02B 6/4298* (2013.01); *G02B 6/4413* (2013.01)

(56) References Cited

U.S. PATENT DOCUMENTS

| | | | |
|---|---|---|---|
| 5,463,712 A * | 10/1995 | Cawood | A61B 1/00181 385/117 |
| 5,730,702 A | 3/1998 | Tanaka et al. | |
| 8,145,018 B2 | 3/2012 | Shishkov et al. | |
| 2006/0235276 A1 * | 10/2006 | Takase | A61B 1/00174 600/177 |
| 2008/0132834 A1 * | 6/2008 | Melville | A61B 1/00172 604/95.04 |
| 2013/0322109 A1 | 12/2013 | Weiger | |
| 2017/0100024 A1 | 4/2017 | Shahmoon et al. | |

FOREIGN PATENT DOCUMENTS

| | | |
|---|---|---|
| JP | 2010-169715 A | 8/2010 |
| JP | 2017-505667 A | 2/2017 |
| WO | 2017/139657 A1 | 8/2017 |

OTHER PUBLICATIONS

JP Notification of Reasons for Refusal issued in related application No. JP2019-010751 dated Jun. 24, 2020 and Google translation.

Yelin, D., et al., "Three-dimensional miniature endoscopy", Nature, Oct. 19, 2006, p. 765, vol. 443.

Tearney, G.J., et al., "Spectrally encoded miniature endoscopy", Optics Letters, Mar. 15, 2002, pp. 412-414, vol. 27, No. 6.

Pitris, C. et al., "A GRISM-based probe for spectrally encoded confocal microscopy" Optics Express, Jan. 27, 2003, pp. 120-124, vol. 11, No. 2.

* cited by examiner

Distal End view

Far field at Wd

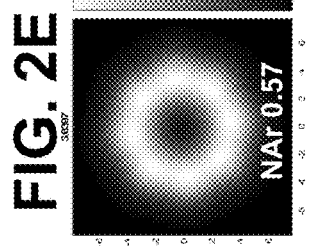
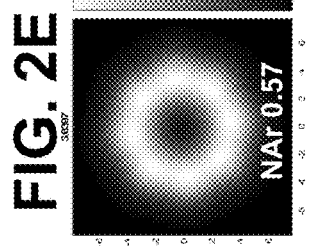
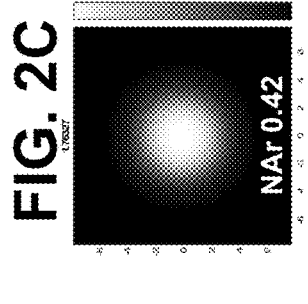
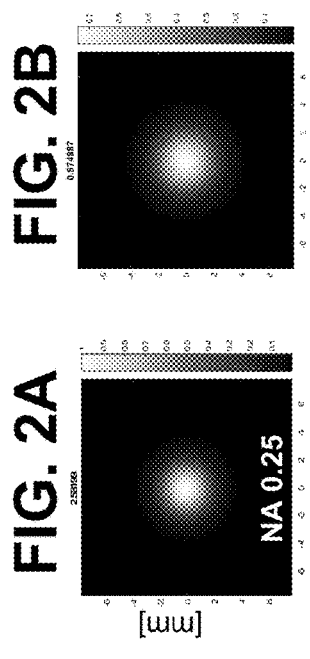
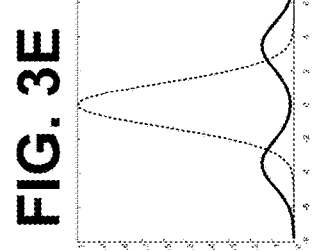
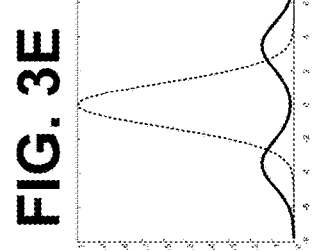
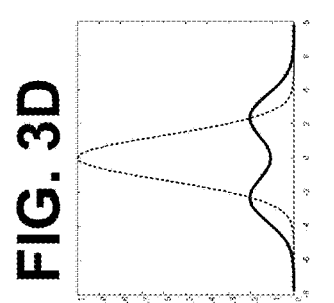
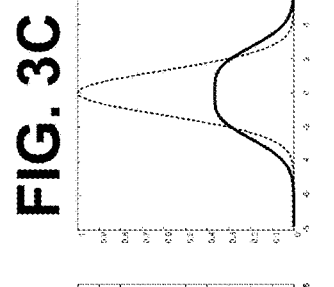
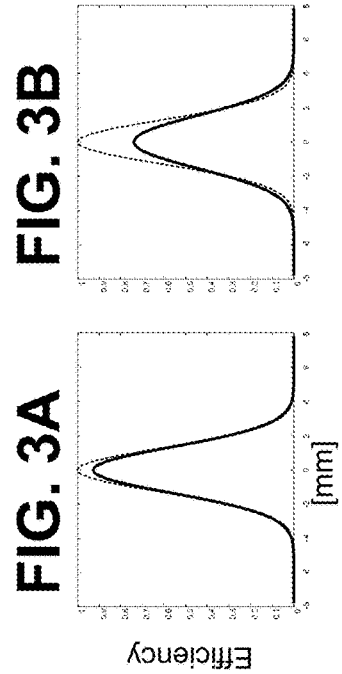
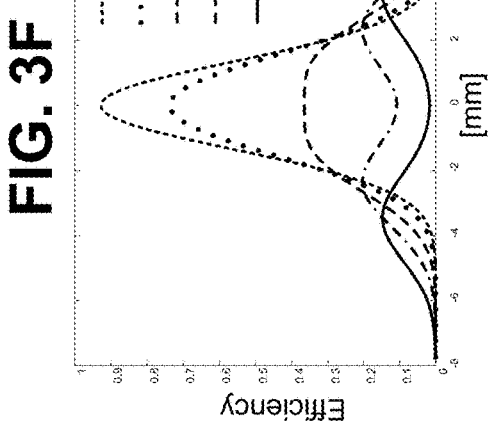

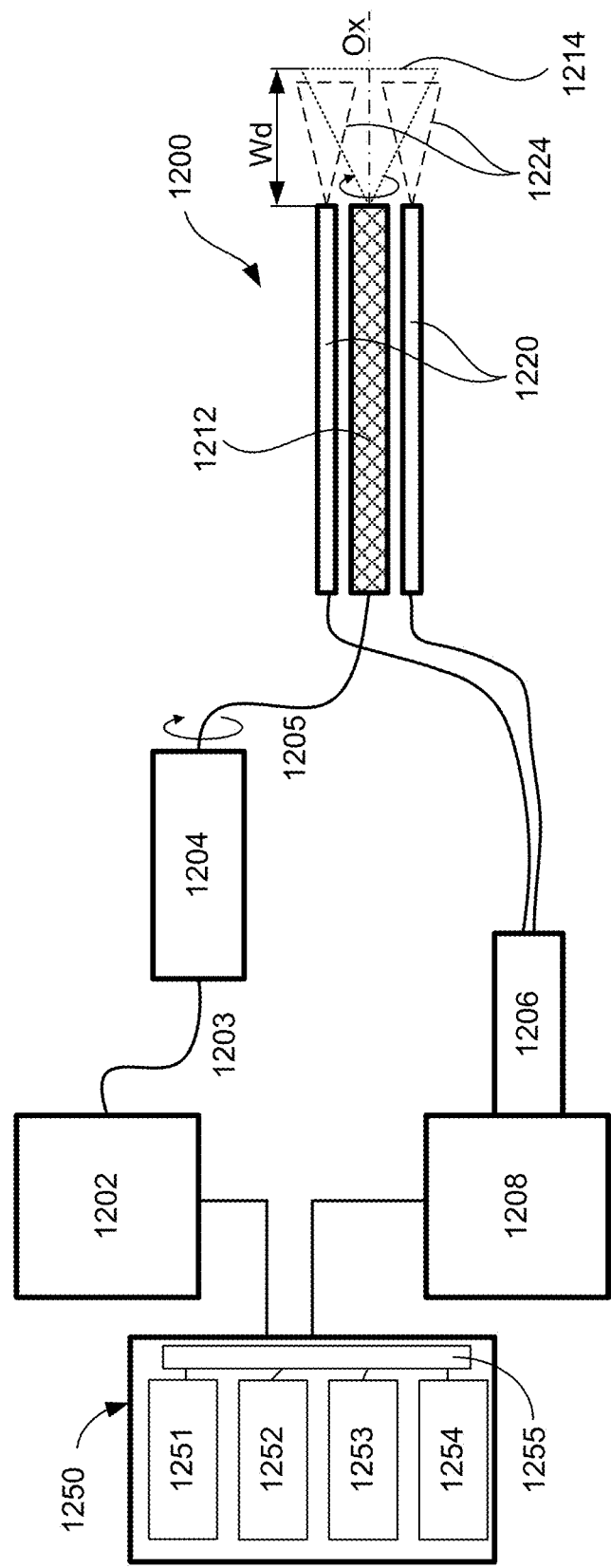

OPTICAL FIBER ARRANGEMENT FOR ENDOSCOPE

CROSS-REFERENCE TO RELATED APPLICATIONS

This application claims priority to U.S. Provisional Application Ser. No. 62/621,945 filed Jan. 25, 2018, the contents of which is herein incorporated by reference in its entirety.

FIELD OF THE DISCLOSURE

The present disclosure generally relates to endoscopes. More particularly, the disclosure exemplifies optical fiber arrangements for endoscopic probes.

BACKGROUND

Medical endoscopic probes have the ability to provide images from inside a patient's body. One useful medical probe employs spectrally encoded endoscopy ("SEE"), which is a miniature endoscopy technology that can conduct high-definition imaging through a sub-mm diameter probe. In a SEE probe, broadband light is diffracted by a grating at the tip of an optical fiber, producing a dispersed spectrum of the different wavelengths (colors) on the sample. Light returned from the sample is detected using a spectrometer; and each resolvable wavelength corresponds to reflectance from a different point on the sample. Thus, a SEE probe encodes light reflected from a given point in the sample by wavelength. The principle of the SEE technique and a SEE probe with a diameter of 0.5 mm, i.e., 500 µm have been described by D. Yelin et al., in a publication entitled "Three-dimensional miniature endoscopy", Nature Vol. 443 (7113), 765 (2006). Another similar example is described by G. Tearney et al., in "Spectrally encoded miniature endoscopy", Opt. Lett., 27(6): p. 412-414, 2002. Imaging with SEE can produce high-quality images in two- and three-dimensions.

Spectrally-encoded endoscopy utilizes the ability of a diffraction grating that deflects incident light to a diffraction angle according to wavelength. When the deflected light hits an object, light is scattered by the object. Detecting the scattered light intensity at each wavelength is equivalent to detecting the intensity from the corresponding diffraction angle. Thus, one-dimensional line image of the object is obtained. A two-dimensional image is obtained by rotating the SEE probe. A three-dimensional image can be obtained by rotating and translating (moving linearly) the SEE probe. Moreover, when incorporated into a sample arm of an interferometer, the SEE probe can also acquire depth information from a sample (e.g., tissue).

Side-viewing and forward-viewing SEE probes are known. In a side-viewing SEE probe, as the grating deflects the light, the incident light is usually bent with respect to the optical axis of the probe. In this manner, no light goes straight with respect to the optical axis of the probe. As no light goes straight, it is not possible with conventional spectrally-encoded endoscopy configuration to view in a forward direction.

In recent years, spectrally-encoded endoscopy probes exhibiting forward viewing characteristics have been disclosed. Forward view SEE probes are preferable for many applications. Forward view SEE is particularly advantageous for applications such as orthopedics, ear, nose and throat (ENT), laparoscopy, and pediatric surgery. The forward view or front-view SEE probe consists of multiple components including lenses, spacer elements, prisms and gratings, which makes the probe design costly and complicated. Examples of such designs can be found, for example, in C. Pitris et al., "A GRISM-based probe for spectrally encoded confocal microscopy", Optics Express, vol. 11, No. 2, pp. 120-124; Jan. 27, 2003 and U.S. Pat. No. 8,145,018, both of which disclose a dual prism configuration where a grating is sandwiched between two prisms (a "grism"). This grism directs spectrally dispersed light in the directions including the optical axis of the fiber. The grism consists of multiple components (grating, prisms) which need proper alignment. The need of a grism to construct a forward-view probe increases the cost, complexity of fabrication and size of the probe.

In patent application publication US 2017/0100024, Shahmoon et al. discusses the use of multiple fibers in a ring configuration for illumination and also discusses changing of the angle by the use of prisms. The use of multiple fibers for endoscopic illumination has also been disclosed by Tanaka et al., in U.S. Pat. No. 5,730,702. International patent application publication WO/2017/139657 also discloses a forward-viewing SEE probe having a plurality of light collecting fibers whose distal ends surround an illumination fiber.

However, for a SEE endoscope system, the entrance of light to the spectrometer is limited to small numerical aperture (NA), while the collection of light from the sample is desired to have large NA for a wide field of view that is illuminated by the illumination optics. In that regard, in U.S. Pat. No. 4,736,734, Matsuura et al. discusses a movable lens system in front of the illumination fibers to change the NA, or the field covered by the illumination.

Accordingly, these known designs of forward view SEE probes have drawbacks. First, the forward view design may not allow for the use of the full available aperture. A smaller aperture means a decreased achievable resolution. Second, these known designs need a refractive surface (e.g., a spacer or lens). Therefore, considering the miniature size of the spacer or lens, and, in particular, the need for alignment of such miniature optics, it is not easy to fabricate a forward viewing SEE probe. Additionally, even when proper fabrication is achieved, these probes often suffer from other challenges, such as cross-talk between the excitation and detected light or the loss of field of view due to limited NA.

Specifically, on one hand, it is desirable to have large NA coverage (e.g. NA=0.5) at the detection side (distal end) of the multiple-fiber array to collect as much light as possible. However, at the spectrometer side (proximal end), it is desirable to have a small NA (about 0.2) to efficiently couple only the collected light onto the spectrometer's entrance slit. Therefore, if the known configuration of a ring-fiber array was used with one type of fiber with a certain acceptance NA, that NA needs to be either large NA of 0.5 to capture the full field of the imaging, but would get lower coupling efficiency at the entrance to the spectrometer. If multimode fibers with low NA of 0.2 were to be used, the NA of the fiber would limit the collection NA, and this would limit the field of view at the imaging side. Typically, the acceptance NA on the collection end of the fiber has a distribution where the higher NA within the acceptance NA has lower coupling efficiency at the periphery, while the coupling efficiency to the fiber at the center of the NA has large coupling efficiency.

Another issue is that the center of the field has relatively higher illumination and scattering coming back to the endoscope due to specular reflection while at higher angles of detection, illumination and scattering from object are low, in addition to significant loss in the system. It is desired to change the distribution of collection efficiency from the fiber's original acceptance distribution to increase the collection efficiency at higher detection angles and reduce collection efficiency in the center of the field (lower detection angle).

Accordingly, it is beneficial to address and/or overcome at least some of the deficiencies indicated herein above, and to provide a new SEE probe having forward direction view, and an apparatus to use such a probe.

SUMMARY

According to at least one embodiment of the disclosure, an endoscopic probe includes a first waveguide enclosed within an inner sheath and extending from the proximal end to the distal end along an axis of the inner sheath; a plurality of second waveguides having at least the distal ends thereof arranged around the inner sheath to surround the distal end of the first waveguide, wherein, at the distal end, the axis of each of the second waveguides is tilted with respect to the axis of the first waveguide by a predetermined angle.

According to other embodiments, there is provided an apparatus comprising a spectrally encoded endoscopy probe extending from a proximal end to a distal end thereof, and configured to be inserted in a tubular lumen to observe a sample, the probe comprising: a first optical fiber enclosed within an inner sheath and extending from the proximal end to the distal end along an axis of the inner sheath; and a plurality of second optical fibers having at least the distal ends thereof arranged around the inner sheath to surround the distal end of the first optical fiber. In this manner, at the distal end, the axis of each of the second optical fibers is tilted with respect to the axis of the first optical by a predetermined angle.

These and other features, and advantages of the present disclosure will become apparent to those skilled in the art upon reading the following detailed description of exemplary embodiments, when taken in conjunction with the appended drawings, and provided claims.

BRIEF DESCRIPTION OF DRAWINGS

FIGS. 2A through 2E illustrate light intensity distribution at the far field various angles of inclination.

FIGS. 3A through 3E illustrate graphs of light collection efficiency at various angles of inclination. FIG. 3F is a graph illustrating a progression of the detection efficiencies at various angles of inclination.

FIG. 12 illustrates a schematic of an exemplary imaging system.

DETAILED DESCRIPTION OF EMBODIMENTS

Figures 1A, 1B, 1C:
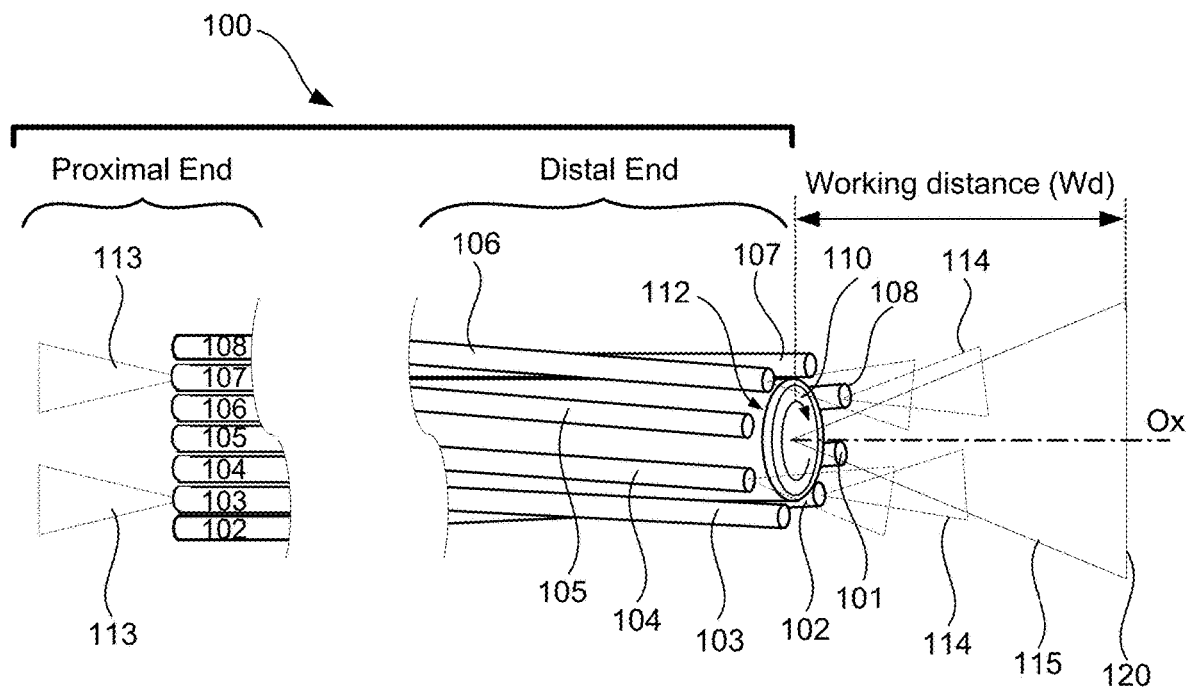
FIG. 1A illustrates an exemplary SEE probe according to an embodiment of the present disclosure.
FIG. 1B illustrates a distal end view of the exemplary SEE probe shown in FIG. 1A.
FIG. 1C illustrates an exemplary representation of light distribution at the far field of the distal end of the exemplary SEE probe shown in FIG. 1A.

Further objects, features and advantages of the present disclosure will become apparent from the following detailed description when taken in conjunction with the accompanying figures showing illustrative embodiments of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

The disclosure of the present application describes various embodiments of an endoscopic probe that uses low NA fibers and effectively increases the collection NA, so that there will be less loss at the spectrometer or detector entrance and still has increased field of view. Throughout this document the numerical aperture NA at the detection end of the endoscope, collection angle, field angle, and field of view are used interchangeably. This is done by lining up the arrays of fibers in helically twisted arrangement at the end of the scope.

To avoid lengthy and unnecessary information, the detailed configuration of a SEE system is omitted here, but a brief description will be provided as an exemplary application of the endoscopic probe. As it is known to those skilled in the art, a SEE endoscopic system generally includes a light source, a rotary junction, an illumination fiber connected to the rotary junction with distal optics which has a dispersive element, detection fibers arranged around the illumination fiber, a spectrometer/detector, and a processor.

Forward-Viewing SEE Probe Structure

FIGS. 1A, 1B, and 1C show the structure and far field light distribution of an exemplary SEE probe 100 according to an exemplary embodiment of the present disclosure. FIG. 1A shows an abbreviated perspective view of an exemplary endoscopic probe 100. FIG. 1B shows a cross-sectional view of the probe 100 seen from the distal end. FIG. 1C shows a far-field spatial distribution of illumination and collection light formed at a working distance Wd from the distal end of the probe 100. As shown in FIG. 1A, the probe 100 includes a proximal end and a distal end extending along an optical axis (Ox).

FIG. 1A shows the probe 100 includes an inner sheath 112 with a rotatable illumination fiber 110 (a first waveguide) disposed inside the inner sheath 112. At the distal end, the detection fibers 101, 102, 103, 104, 105, 106, 107, and 108

(a plurality of second waveguides) are arranged concentrically in a ring pattern around the inner sheath 112 and inside an outer sheath 118, as shown also in FIG. 1B. Each of the detection fibers 101 to 108 has a cone of NA 114 at the distal end to collect light from a far field 120 at a working distance (Wd), and a cone of NA 113 at the proximal end to match the acceptance NA of the spectrometer. The detection fibers 101 to 108 are wrapped around the inner sheath 112 in a helical manner, such that each fiber is helically wound next to each other around the outer surface of the inner sheath 112. As a result, at the distal end of the endoscope, each of the detection fibers 101 to 108 is tilted with respect to the axis Ox of inner sheath 112 at a predetermined angle T. Preferably the fibers 101 through 108 are arranged symmetrically around the inner sheath 112, and all fibers are tilted, so that their cones of acceptance NA 114 will be tilted by the predetermined angle with respect to the axis Ox. As explained more in detail herein below, the cones of acceptance NA 114 are tilted by the predetermined angle pointing away from the optical axis Ox.

The inner sheath 112 houses the rotatable illumination fiber 110 with sufficient tolerance to avoid friction during rotation, while maintaining the optical axis of illumination fiber 110 substantially aligned (parallel) with the axis Ox of the inner sheath 112. The illumination fiber 110 has a cone of illumination 115 such that, in the far field 120, an area of a sample (not shown) is covered by a large circular field of view 129 (solid line shown in FIG. 1C). In addition, each cone of NA 114 of the detection fibers 101, 102, 103, 104, 105, 106, 107 and 108 respectively covers a small field 121, 122, 123, 124, 125, 126, 127 and 128, as shown in FIG. 1C. As a result of all the fibers 101 to 108 being symmetrically tilted around the inner sheath 112, the detection fibers 101 through 108 effectively cover a full field of view 130 having an area larger than the circular field of view 129. Therefore, the effective a numerical aperture NA of the detection fibers 101 through 108 is larger than the NA of the cone of illumination 115.

In FIG. 1A, the parts of the endoscope between the distal end and the proximal end proximal are not shown for ease of illustration. It should be understood however that omitted elements, such as a fiber rotary joint (FORJ) for connecting the illumination fiber 110 to its optical source and other elements, are considered to be included in the endoscope of probe 100. Notably, along the length of the endoscope, the detection fibers 101 to 108 are separated from the inner sheath 112, so that the illumination fiber 110 is directed to a light source (not shown) and the detection fibers are directed to a spectrometer. The arrangement of the detection fibers 101 to 108 on proximal end (detector side) is further configured to fit the detector. Specifically, as shown in FIG. 1A, at the proximal end, the fibers are arranged in one line for spectrometer input for spectrally encoded endoscopy. The line direction corresponds to the slit direction of the spectrometer in common use.

FIGS. 2A through 2E show results of detection of light from far field light intensity distribution at a working distance (Wd) of 10 mm. For these results it is assumed the use of a fiber of NA 0.25 and a Gaussian distribution at $1/e^2$. FIG. 2A shows detection of light intensity distribution (using a fiber NA=0.25) for a case where all the detection fibers are arranged in a circle and all parallel (angle of inclination zero) to the axis of the inner sheath 112. FIG. 3A shows the collection efficiency distribution (solid line) corresponding to the detected light intensity results shown in FIG. 2A compared to the standard Gaussian distribution (dashed line). FIG. 2B shows detection of light intensity distribution (using a fiber NA=0.25) for a case where all the detection fibers are arranged tilted with an angle of inclination of 5 degrees with respect to the axis of the inner sheath 112. FIG. 3B shows the collection efficiency distribution corresponding to the detected light intensity results shown in FIG. 2B. FIG. 2C shows detection of light intensity distribution (using a fiber NA=0.25) for a case where all the detection fibers are arranged tilted with an angle of inclination of 10 degrees with respect to the axis of the inner sheath 112. FIG. 3C shows the collection efficiency distribution corresponding to the detected light intensity results shown in FIG. 2C. FIG. 2D shows detection of light intensity distribution (using a fiber NA=0.25) for a case where all the detection fibers are arranged tilted with an angle of inclination of 15 degrees with respect to the axis of the inner sheath 112. FIG. 3D shows the collection efficiency distribution corresponding to the detected light intensity results shown in FIG. 2D. FIG. 2E shows detection of light intensity distribution (using a fiber NA=0.25) for a case where all the detection fibers are arranged tilted with an angle of inclination of 20 degrees with respect to the axis of the inner sheath 112. FIG. 3E shows the collection efficiency distribution corresponding to the detected light intensity results shown in FIG. 2E.

With the detection fibers having a 10 degrees angle of tilt with respect to the axis of the inner sheath 112, and the fiber ends arranged in a ring pattern of a circle of diameter of 1 mm, the distribution is shown in FIG. 2C with resultant or effective NA (NAr) of 0.42. FIG. 3C shows the cross sections of the distribution of FIG. 2E (solid line graph) compared to the standard Gaussian distribution (dashed line graph). The efficiency is normalized so that the center is 1 for no-tilt orientation. In FIG. 3C, it can be appreciated that because the center of the field is not collected by the center of the view of each of the fibers, the efficiency is lower than no-tilt orientation. However, in FIG. 3C it can also be appreciated that the collection efficiency improves in the peripheral region of the field.

FIG. 3F shows the progression of the detection efficiency distributions in the field of view for the fiber tilt of 0, 5, 10, 15, 20 degrees, respectively for a probe having 8 detection fibers. NA of the fiber is 0.25. The working distance of field of view illustrated is at 10 mm. The fiber tip is arranged on a circle with a radius of 0.5 mm and oriented at the indicated tilt angle away from the axis Ox. (Assuming approximate diameter of 1 mm for the inner sheath 112). FIG. 3F shows the cross sections of the distributions at the central horizontal line of FIGS. 2A to 2E. The single Gaussian profile overlapped is the efficiency from all 8 fibers overlapped, without any tilt (0 Deg.). The detection efficiency distribution of 0 Deg. tilt is slightly lower than 1 (the standard Gaussian distribution) because the fiber tips are arranged on a circle with a radius of 1 mm.

The foregoing effects that a change in fiber tilt inclination can have on the collection efficiency can also be applied to illumination efficiency. These effects can be expressed mathematically to advantageously determine a proper arrangement of fibers for the endoscopic optical probe.

Specifically, when the fiber NA is NAf and the fiber tilt angle is T, then the effective or resultant NA, defined as NAr, can be expressed as follows:

$$NAr = \sin(\arcsin(NAf) + T) \qquad \text{Equation (1)}$$

Or, in order to have the resultant expanded NA of NAr the tilt angle T is defined as follows:

$$T = a\sin(NAr) - a\sin(NAf) \qquad \text{Equation (2)}$$

For an arrangement of 8 fibers of NA 0.25, tilted with 20 degrees tilt with respect to the axis of the inner sheath 112, the effective far field intensity distribution at working distance of 10 mm is shown in FIG. 2E. The collection efficiency (solid line) shown in FIG. 3D is compared to the standard Gaussian distribution (dashed line). The efficiency is normalized so that the center is 1 for no-tilt orientation. Because the center of the field is not collected by the center of the view of each of the fibers but rather collected with the periphery of the fiber acceptance NA, the efficiency is low at center, but increases in the periphery of the field. This results in an increase of the effective NA. For FIGS. 2E and 3E as shown in this embodiment the effective NA (NAr) is 0.57, with the central portion considerably low on detection efficiency. This central portion having low detection efficiency can effectively act as an obscuration portion in the far field light distribution. In order not to have a central obscuration of no detection at all, the tilt angle T can be limited by the following equation:

$$T < a\ \sin(NAf) \qquad \text{Equation (3),}$$

where NAf is the acceptance NA of the fiber.

Multimode fibers often have collection efficiency with wider distribution closely resembling a top hat distribution instead of Gaussian distribution, as discussed above. Therefore, in an exemplary embodiment, multimode detection fibers with an intensity distribution having a profile closer to a top hat distribution may be used. In this manner, it is possible to increase the collection efficiency in the center of the field even when the fibers are tilted at up to 20 degrees with respect to the axis Ox.

Another exemplary design uses multimode fiber of NAf 0.64 which corresponds to a cone of acceptance with half angle of 40 degrees. In order to cover a field of view of 110 degrees (effective NA:NAr 0.82), a tilt angle T of the fibers at the distal end is set to 15 degrees. The same fibers are tilted to the tilt angle of T at 5 degrees to cover the field of view of 90 degrees (NAr of 0.71). Yet another exemplary design uses multimode fiber of NM 0.55, which corresponds to cone of acceptance with half angle of 33 degrees. In order to cover field of view of 90 degrees (effective NA:NAr 0.71), a tilt angle T of the fibers is adjusted to 12 degrees. The same fibers are tilted further to tilt angle T at 22 degrees to cover the field of view of 110 degrees (NAr of 0.82).

In an embodiment, it is preferable to arrange detection fibers such that the tilt plane of each fiber is tangential to the edge (distal tip) of the inner sheath at the tip of the fibers. FIGS. 13A through 13D are used to explain the direction of the tilt of the fiber axis and the viewing direction. In FIG. 13A, the inner sheath 112 is shown as a three-dimensional cylindrical structure with a plane 1302 tangent to the outer surface at the tangent line 1303. The detection fiber 1304 is tilted in the plane 1302, such that the viewing axis 1305 of the fiber is also tilted in the plane 1302, but the viewing axis 1305 is not parallel to the tangent line 1303. If the fiber thickness is assumed to be negligible (e.g., assuming the fiber radius to be a few microns), the fiber 1304 and the viewing axis 1305 are on the tangent plane 1302. Since the tangent line 1303 is parallel to the axis Ox of the inner sheath 112, the tilt angle T may be considered as the angle between the viewing axis 1305 (axis of fiber 1304) and the tangent line 1303 on the tangent plane 1302. FIG. 13A shows the distal end of fiber 1304 is tilted with respect to the distal end of the inner sheath 112. However, as shown and explained in reference to FIG. 7, it may be simpler to adjust the fiber end flush with the distal end of the inner sheath by polishing together the fiber and sheath after arranging the fiber around the central lumen.

Figure 13B:
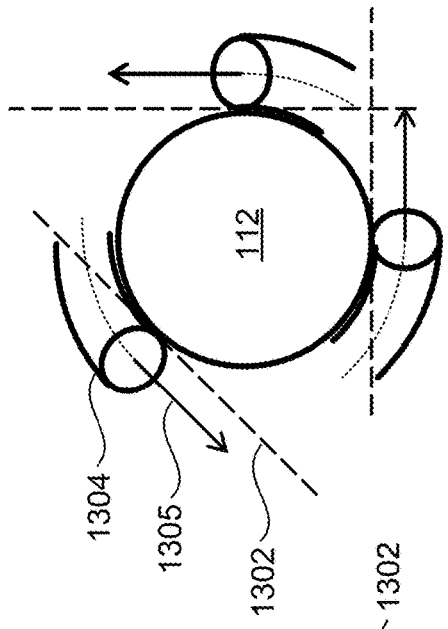
FIGS. 13A through 13D are schematic diagrams showing the distal end of an endoscopic probe used to explain the direction of the tilt of the fiber axis and the viewing direction.
Figure 13D:
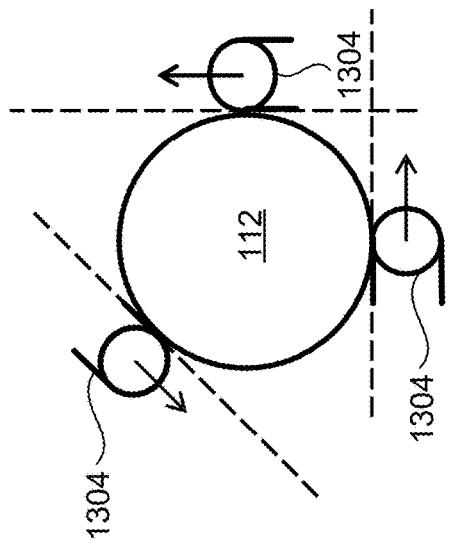
Figure 13C:
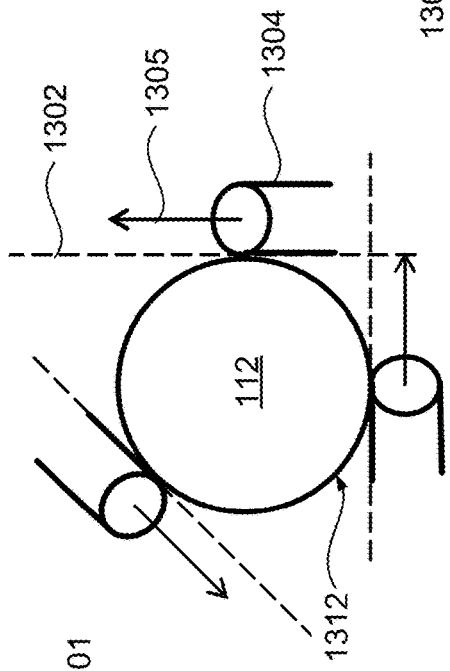
Figure 13A:
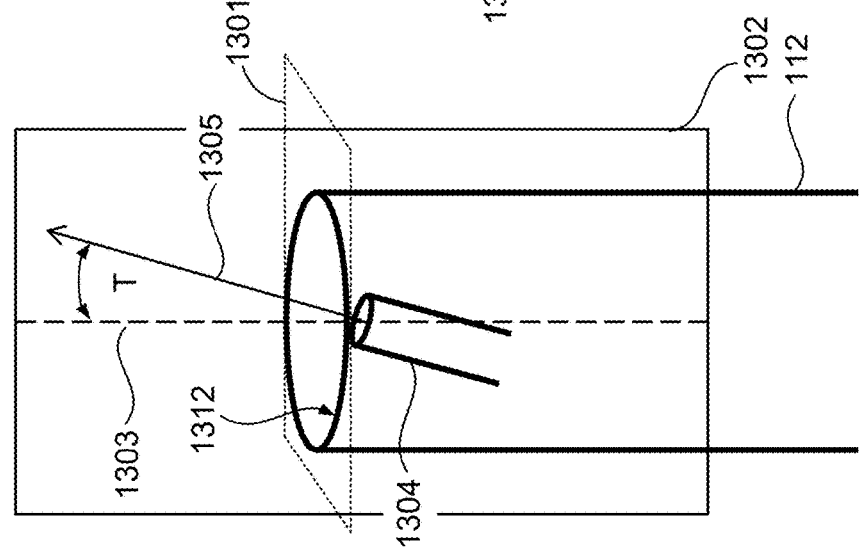

FIG. 13B shows the top view (front view) of the configuration shown in FIG. 13A with three example fibers 1304 helically and tightly wound around the outer surface of inner sheath 112. FIGS. 13C and 13D show additional views of the distal ends of the fibers 1304 wrapped around the inner sheath 112 in a helical manner. Each of the three fibers 1304 shows its respective tangent plane 1302 to the central tube by the dashed line and the viewing axis 1305 with an arrow. FIG. 13D shows the fibers with less tilt than in FIG. 13C. As understood from FIG. 3B, although the viewing axis 1305 follows a helical locus around the outer surface of the inner sheath 112, at the distal edge 1312 of the inner sheath 112, the viewing axis 1305 of the fiber simply extends along (parallel to) the tangent plane 1302. Here, the distal edge 1312 is a circle (the outer surface of the inner sheath) in a plane 1301 perpendicular to the axis Ox of inner sheath. The projection of the fiber viewing axis 1305 to that perpendicular plane is approximately or substantially tangent to the edge 1312 (assuming the fiber diameter is a few microns or negligible). Therefore, the distal ends of the optical fibers 1304 are tilted with respect to the axis of the inner sheath in a manner such that, at the distal end of the inner sheath, the axis 1305 of each fiber is substantially tangent to the distal edge 1312 of the inner sheath 112, in the plane 1301 perpendicular to the axis of inner sheath. In this manner, the ring of fibers 1304 forms an effective cone of acceptance having the above-described NAr.

Other Fiber Arrangements

Two layers of fibers with different tilts.

Figure 4A:
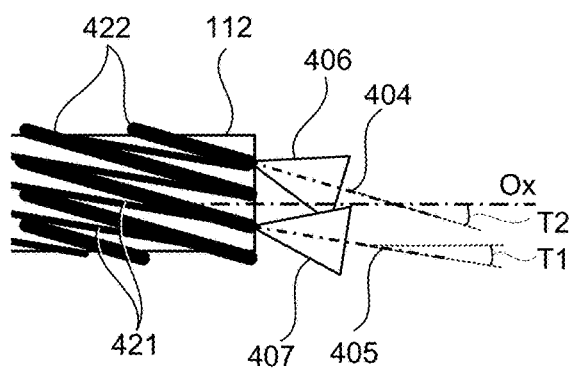
FIG. 4A illustrates an embodiment of a forward view SEE probe having two layers of fibers with different angles of tilt.
Figure 4B:
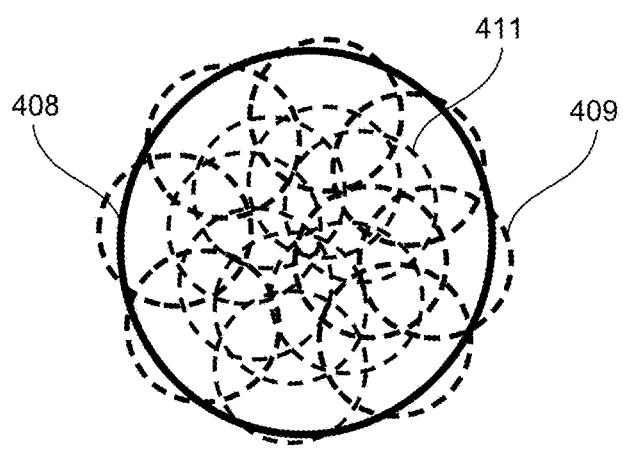
FIG. 4B shows the far field pattern of the SEE probe shown in FIG. 4A.
Figure 4C:
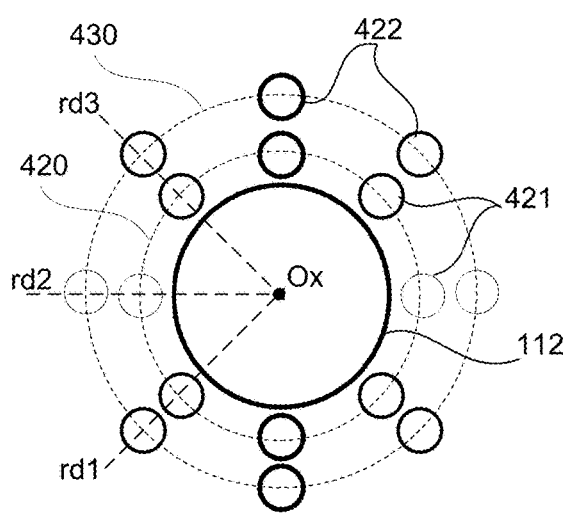
FIG. 4C and FIG. 4D show exemplary arrangements of the multiple fibers of the SEE probe shown in FIG. 4A, as seen from the distal end.
Figure 4D:
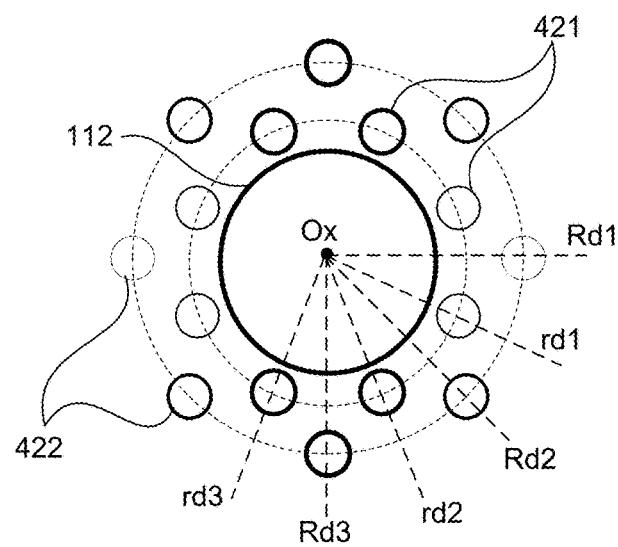

FIG. 4A shows the configuration of an exemplary embodiment of a distal end of an endoscope having two layers of fibers with different tilts. FIG. 4B shows the far field distribution pattern at the working distance of 10 mm. FIGS. 4C and 4D show two different possible arrangements of the detection fibers seen from the distal end. In this embodiment, fibers are arranged in two layers in two rings patterns around the inner sheath 112. Each layer has different angle of tilt. The first layer 420 is an inner layer of eight detection fibers 421, which are shown with thinner lines on the side view of FIG. 4A. These fibers 421 are tilted with a small angle such that the axis 405 of each fiber 421 in the inner ring makes a first angle T1 with respect to the axis Ox of the inner sheath 112. The second layer 430 is an outer layer of eight detection fibers 422, which are shown with thicker lines on FIG. 4A. These fibers 422 are tilted at a second angle T2 larger than the angle T1 of inner layer fibers such that the axis 404 of each fiber 422 at the tip of the sheath makes a larger angle with the axis Ox of the inner sheath 112. Each fiber 421 in the first layer 420 has an acceptance cone 407, and each fiber 422 in the second layer 430 has an acceptance cone 406.

FIG. 4B shows the far field distribution pattern of the field of view. The illumination field of view covered by the illumination light is shown by a solid line circle 408. The cone 407 of detection NA for the inner layer fibers 421 with smaller tilts (with respect to the axis Ox) are shown with dashed line 411 with the circles closer to the center of the far field distribution. The cone 406 of detection NA for the outer layer fibers 422 with larger tilts (with respect to the axis Ox) are shown with dashed line 409 with the circles positioned farther from the center covering the periphery of the field of illumination 408 (solid dark line).

FIGS. 4C and 4D show exemplary arrangements of the two-layer fiber tips seen from the front (distal end) of the endoscope. In one configuration shown in FIG. 4C, the inner layer fibers 421 are arranged in contact with an inner sheath 112 at the same rotational angle as outer layer fibers 422. That is, as shown in FIG. 4C, the fibers 421 in the first layer 420 and the fiber 422 in the second layer 430 aligned along a common radial direction rd1, rd2, rd3, etc. In another configuration shown in FIG. 4D, the inner layer fibers 421 are arranged around the inner sheath 112 at the different rotational angle than the outer layer fibers 422. Specifically, as shown in FIG. 4D, the fibers 421 in the first layer 420 can be arranged in radial directions rd1, rd2, rd3, etc., while the fibers 422 in the second layer 430 are arranged in radial directions Rd1, Rd2, Rd3, etc. where are rd1≠Rd1, rd2≠Rd2, rd3≠Rd3, such that the fibers 421 are radially staggered with respect to fibers 422.

Figure 5:
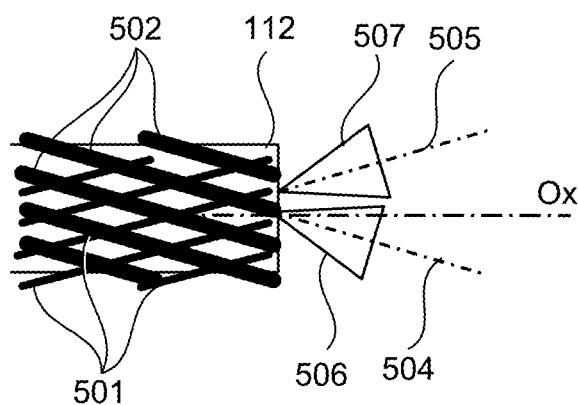
FIG. 5 illustrates an embodiment of a forward view SEE probe having two layers of fibers with opposite angle of tilt.

FIG. 5: Two Layers of Fibers With Opposite Tilt

In the embodiment of FIG. 5, detection fibers are arranged in two layers around the inner sheath 112 (central lumen) with opposite tilt. Each layer has the same angle of tilt but tilted in the opposite direction. The first or inner layer includes a plurality of detection fibers 503 which are shown with thinner lines on the side view of FIG. 5. These fibers 503 are tilted with a specific designed angle T1 such that each fiber axis 505 makes a small angle with the axis Ox of the inner sheath 112. The second or outer layer includes a plurality of detection fibers 502 which are shown with thicker lines on FIG. 5. These fibers 502 are tilted in an opposite direction with respect to the fibers 501 such that the fiber axis 504 of each fiber 502 makes substantially the same designed angle T1 but in opposite direction with respect to the axis Ox of the inner sheath 112. In this manner, each fiber 201 in the first layer has an acceptance cone 507, and each fiber 502 in the second layer has an acceptance cone 506.

In the far field pattern, not shown, the cone 507 of detection NA for the inner layer fibers 501 covers the same radius from the center of the field of view as the cone 506 of detection NA for the outer layer fibers 502.

This configuration increases the light collection efficiency by having more detection fibers, and it can reduce any possible central or asymmetric shadowing effect that could be present by single layer detection.

Figure 6:
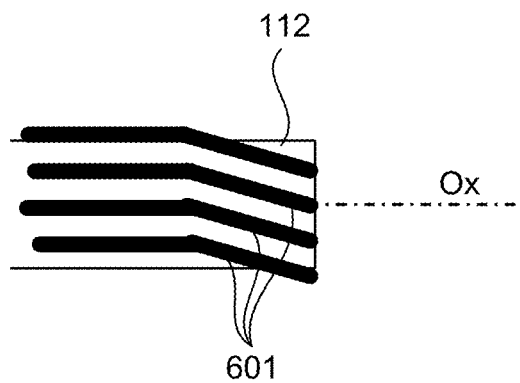
FIG. 6 illustrates an embodiment of a forward view SEE probe having multiple fibers tilted only at the distal end of the probe.

FIG. 6: Fibers Tilted Only at the Distal End of the Probe

FIG. 6 shows the configuration of another embodiment with the detection fibers extending substantially parallel to the inner sheath and then being tilted only at the distal end. Although the detection fibers in the previous embodiments could wrap around the outer surface of the inner sheath in helical manner all along the length on the central lumen, it does not have to be. This embodiment shown in FIG. 6 has the detection fibers 601 configured parallel to the inner sheath 112 (central lumen) to the location close to the tip, and then the fibers are tilted only at or near the tip of the inner sheath.

Figure 7:
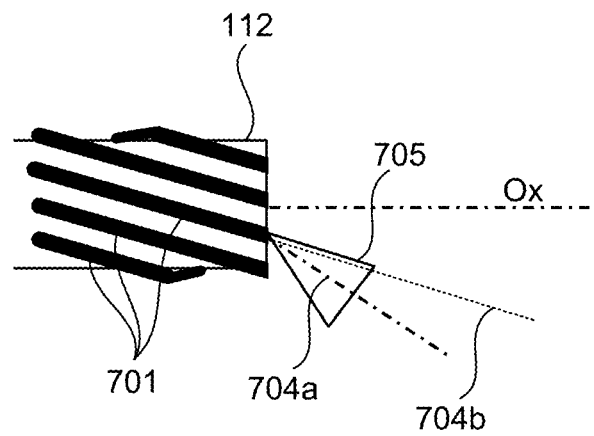
FIG. 7 illustrates an embodiment of a forward view SEE probe having the tips of a plurality of fibers polished perpendicular to the axis of the inner sheath.

FIG. 7: Fiber Tip Perpendicular to the Axis of the Inner Sheath

The previously explained embodiments are explained as the field of view of each fiber being aligned to the tip axis of the fiber at the tip. In the assembly process, it is often simpler to adjust the multiple fiber length flush at the tip by polishing together after arranging the fiber around the central lumen. FIG. 7 depicts the configuration made by this method. In FIG. 7, a plurality of detection fibers 701 are helically wrapped around the inner sheath 112. When assembled and processed in this method, the fiber ends of the fibers 701 will be polished perpendicular to the axis Ox of the sheath 112. In this embodiment, the axis 704a of a collection cone 705 is tilted more (at a larger angle) than the fiber axis 704b with respect to the sheath axis Ox due to refraction at the boundary surface of fiber exit.

Figure 8:
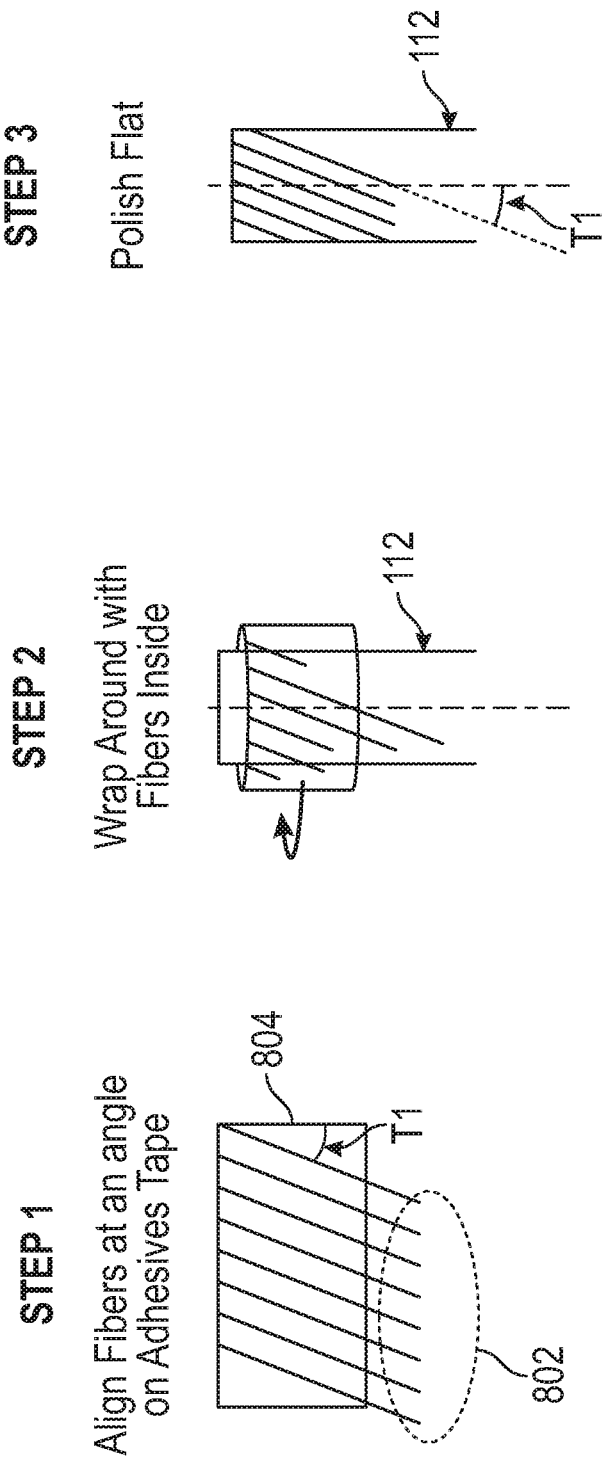
FIG. 8 illustrates a first method of fabrication.

FIG. 8: Method of Fabrication—Wrap and Polish at the End

FIG. 8 depicts a first process of fabrication of a sheath with detection fibers wrapped in a helical manner around the sheath.

STEP 1: First align fibers 802 at a predetermined angle T1 on an adhesive tape 804. STEP 2: Wrap the adhesive tape 804 around a desired tubular structure which is to be the inner sheath 112 that encloses the center fiber. In STEP 2, the fibers 802 can be either outside of the adhesive tape or inside. That is, when the adhesive tape 804 is wrapped around the sheath 112, the fibers 802 are in direct contact with the outer surface of the sheath 112, or the adhesive tape 804 is in direct contact with the outer surface of the sheath 112. If the fibers are outside of the adhesive tape, then it is preferable to have another adhesive tape or heat shrink tubing outside to protect the fibers. Here, it is understood that fibers 802 can be wrapped helicoidally around the sheath 112 along the entire length of the sheath 112. Alternatively, the fibers 802 can be wrapped helicoidally around only the distal end of the sheath 112, for example as shown in FIG. 6.

STEP 3: Once the fibers are wrapped around the sheath 112, the fiber tip (fiber edge) of each fiber is polished to be flush with the front edge of the sheath 112. When the fibers are not aligned in the longitudinal direction (not parallel to the axis of the inner sheath 112), as shown in STEP 1 of FIG. 8, then polishing the assembly altogether flat perpendicular to the axis of the tubular sheath will make the edge (fiber tip) of each fiber perpendicular to the axis of the sheath. This process ensures that all fibers are polished uniformly with the same angle, and also enables faster manufacturing production as compared to polishing the fibers one-by-one and then wrapping them around the sheath. Naturally, the steps 1 and 2 can be repeated for multiple layer configurations, and then step 3 can be performed once.

Figure 9:
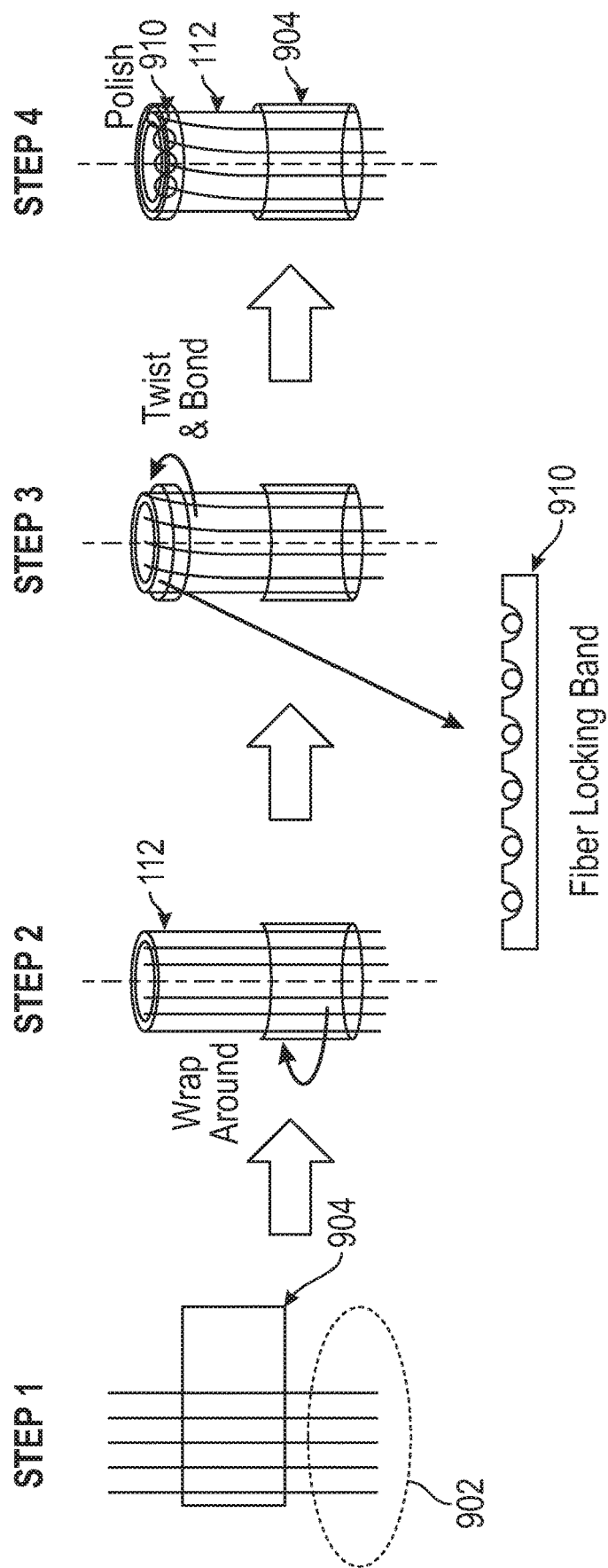
FIG. 9 illustrates a second method of fabrication.

FIG. 9: Method of Fabrication—Tilt Only at the Tip.

FIG. 9 depicts a second process of fabrication of a sheath 112 with detection fibers 902 wrapped around the inner sheath 112 in a helical manner, and tilted only at the distal end thereof.

STEP 1: First align fibers 902 straight and parallel to each other on an adhesive tape 904. The adhesive tape 904 should be located some length from the fiber tip to leave some length at the fiber tip to be loose (not attached to the adhesive tape). STEP 2: Wrap the adhesive tape 904 around the tube which is to be the inner sheath 112 for the central fiber such that the fibers 902 are substantially parallel to the axis of the sheath 112. At this time, the fibers 902 can be either outside of the adhesive tape or inside. If the fibers 902 are outside of the adhesive tape 904, then it is preferable to have another adhesive tape or heat shrink tubing outside to protect the fibers 902. Here, it is understood that fibers 902 can be wrapped parallel to the sheath 112 along the entire length of the sheath 112 from the proximal end to the distal end. Alternatively, the fibers 902 can be arranged around the outer surface of the sheath 112 and parallel to the axis thereof only a certain length at the distal end of the sheath 112.

STEP 3: After the fibers 902 are attached to the outer surface of inner sheath 112, a certain length of the fiber ends are wrapped around the cylindrical surface of the inner sheath 112. This can be done with a fiber locking band 910 (a fiber locking mechanism) which has the profile as shown in the bottom section of FIG. 9. Specifically, the fiber locking band has a profile with openings or grooves for locking each fiber. This fiber locking band 910 is then rotated relative to the inner sheath 112 so as to bend (twist) the fibers around the tip of the sheath at a predetermined angle. Then, the fiber locking band 910 and the fibers 902 are affixed or bonded by adhesives or by a heat shrink tube over them. STEP 4: Then polishing the assembly altogether flat perpendicular to the axis of the tube of inner sheath 112 will make the edge of ach fiber to be perpendicular to the central axis of the sheath 112. As explained above with reference to FIG. 8, steps 1 and 2 can be repeated for multiple layer configurations.

The process for wrapping the fibers around the inner sheath 112 in a helical manner is not limited to the foregoing two exemplary processes. Instead of using adhesives, to ensure a precise positioning of the fibers at the distal end of the inner sheath 112, it is possible to provide the outer surface of the inner sheath 112 with predetermined helical grooves, and to arrange each fiber following a helical path (helical locus) around and in contact with the inner sheath.

Adjusting the Angle of Inclination With Respect to Inner Sheath

Figure 10:
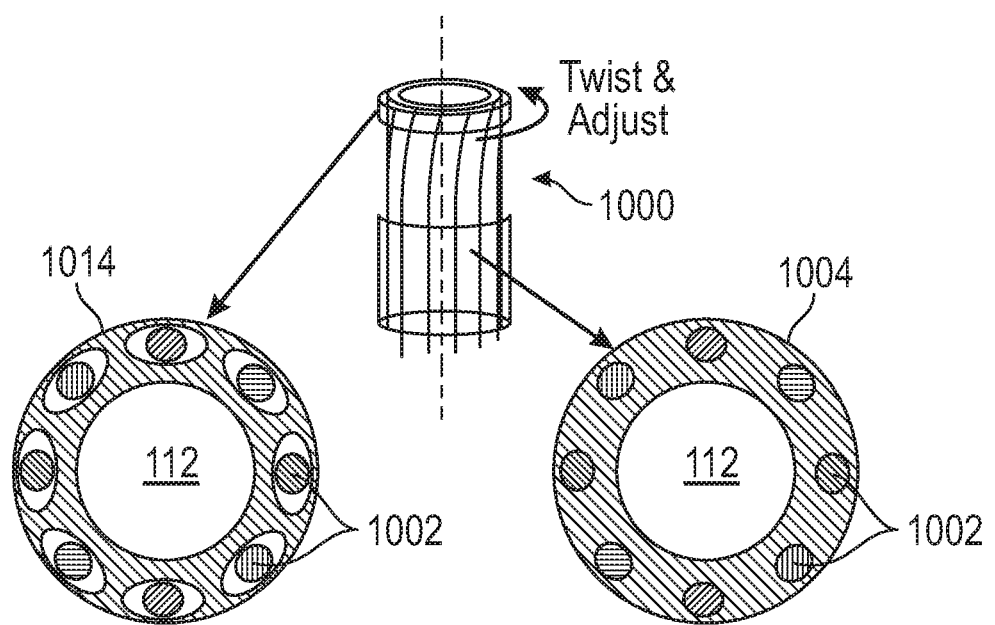
FIG. 10 illustrates method of adjusting an angle of inclination of the multiple fibers with respect to the inner sheath.

FIG. 10 shows an embodiment of an endoscopic probe having a mechanism for dynamically adjusting an angle of fiber tilt with respect to the axis of the sheath 112 even after the probe has been assembled. In FIG. 10, an assembled probe 1000 includes a plurality of fibers 1002 assembled around an inner sheath 112. The sheath 112 has fibers 1002 locked in place at a certain distance from the distal tip (edge) thereof, by either a multi-lumen tube 1004 or alternative adhesives (e.g., an adhesive tape), which tightly locks the fibers 1002 in place. In addition, the sheath 112 has the fibers 1002 loosely fitted around the distal end thereof by a fiber adjusting band 1014. The cross section of the fiber adjusting band 1014 is shown with loose elongated holes for holding fibers 1002. In this manner, by rotating and adjusting the rotational position of the adjusting band 1014 with respect to the inner sheath 112, the tilt angle of each fiber 1002 can be dynamically adjusted. This enables the collection field of each individual fiber to open up or close down in the field of view. When more efficiency is needed to view the central part of the field of view, then the adjusting band 1014 can be rotated to make the fiber axis to be more parallel to the axis of inner sheath 112. This makes the collection cone of the fibers to close down in the field of view to collect light from the central portion more efficiently. When more efficiency is needed for the periphery of the field of view, then the adjusting band 1014 can be rotated in the opposite direction to make the angle of the fiber tilt larger. This makes the collection cone of the fibers to open up in the field of view to collect light from the periphery more efficiently.

Mechanism for Adjusting Angle of Inclination

Figure 11:
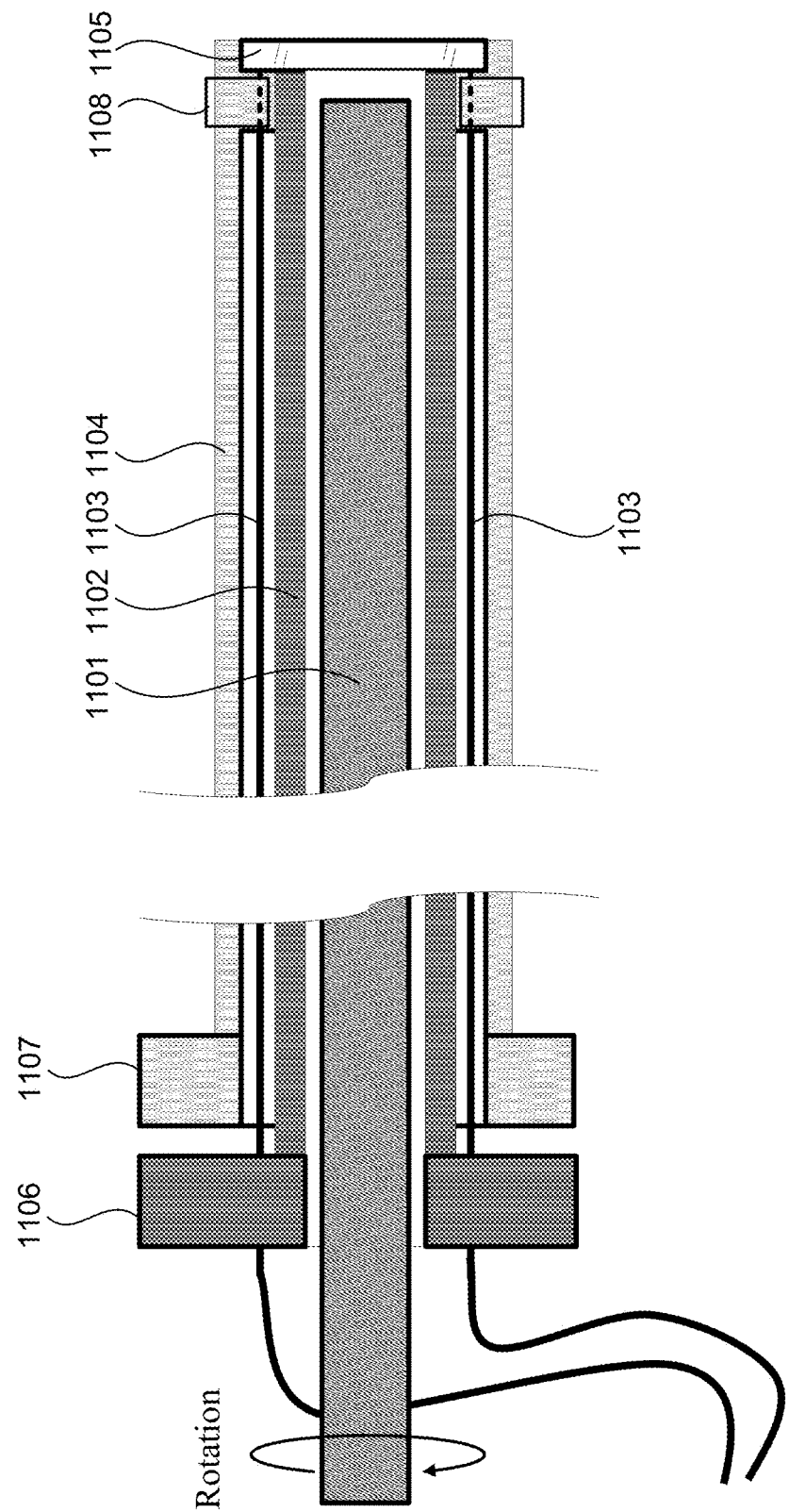
FIG. 11 illustrates a cross-sectional view of a mechanism for adjusting an angle of inclination of the multiple fibers with respect to the inner sheath.

FIG. 11 is a cross sectional view used to further explain the embodiment of adjustable tilt fibers. The rotatable illumination core 1101 is the rotating part which includes thereinside the illumination fiber (not shown). A drive cable (not shown) consisting of one or more wires to transfer the rotation from the motor (not shown) at the proximal end holds the illumination fiber and distal optics inside. A plurality of detection fibers 1103 are attached to a central tube 1102 (inner sheath) except for the very tip where the fibers are to be flexibly tilted. The outer tube 1104 (an outer sheath) has a locking band 1108 attached thereto, but this band 1108 is rotatable with respect to the central tube 1102, and the locking band 1108 holds fibers 1103 loosely by their tips (e.g., as a band 1014 shown in FIG. 10). A transparent window 1105 is attached to the distal end of outer tube 1104.

The central tube 1102 is attached to a back dial 1106 at the proximal end of the probe, and the outer tube 1104 is attached to a front dial 1107 at the proximal end. In this embodiment, the fibers 1103 are arranged concentrically between central tube 1102 and the outer tube 1104, and at the proximal end the fibers 1103 go through the back dial 1106, and then are separated from the probe and arranged in an linear array (as shown in FIG. 1A) to direct the detected light towards the detection unit (e.g., a line sensor and spectrometer). By rotating the front dial 1107 with respect to the back dial 1106, the flexible ends of the fibers 1103 twist at the distal end due to the rotation of locking band 1108. This enables dynamically adjusting the tilt of the fiber tips and thus adjusts the field of view of detection for the SEE endoscope. Similar effect can be obtained by attaching the fibers 1103 to the inner surface of the outer tube 1104 with the flexible ends loosely held in the locking band 1108. The locking band 1108 being attached to the inner tube 1102 and the inner tube being rotatable in this case.

In a conventional endoscope, the central core 1101 is the optical core of the imaging system including most optics, such as fiber bundles, relay lenses or chip-on-tip camera with wires. In the present disclosure, it is advantageous to collection and illumination optics as described above. Although the foregoing embodiments describe collection fibers helically wrapped around the inner sheath such that distal end of the fibers can be tilted with respect to the probe axis, the same novel arrangement can be applied to illumination fibers. In that case, in FIG. 11, Illumination fibers are depicted by 1103 with flexible tips. As the front dial 1107 is rotated with respect to the back dial 1106, then the illumination NA is adjusted. Then, a zoom function of the optics or the image processing can then adjust the illuminated field of view simultaneously.

Imaging System

FIG. 12 illustrates an exemplary imaging system using the endoscopic SEE probe, according to an embodiment of the present disclosure. The system of FIG. 12 includes, for example, an endoscopic probe 1200, a broadband light source 1202, a fiber optic rotary junction FORJ 1204, a spectrometer 1206, a detector 1208, and a computer 1250. A fiber 1203 connects the broadband light source 1202 to the fiber rotary junction 1204. Light then goes from the FORJ 1204 through an optical fiber (illumination fiber 1205); the illumination fiber 1205 extends along an inner sheath 1212 from the proximal end to the distal end of the probe 1200. The rotation of the illumination fiber 1205 along with the rotation of the inner sheath 1212 and a cone of illumination light 1214 is depicted with the circular arrows. The cone of illumination light 1214 is incident on a sample (not shown) at a working distance Wd. A plurality of detection fibers 1220 are arranged to surround the inner sheath 1212 at least at the distal end thereof. The arrangement of the detection fibers 1220 can be implemented according to one or more of the several embodiments described above. Light collected by a cone of acceptance 1224 of each detection fiber 1220 is delivered to the spectrometer 1206 and/or the detector 1208. Specifically, light is sent through the plurality of detection fibers 1220 (e.g., multimode fibers), which, at the proximal end of the probe 1200, are lined up in a linear array at the entrance slit to the spectrometer 1206. The light (dispersed light) is then imaged on the detector 1208. The computer 1250 controls the operations of the light source 1202, FORJ 1204, and detector 1208 to obtain an image of a non-illustrated sample.

In some embodiments, the detector 1208 is a line scan sensor, such as a line scan camera. The line scan sensor may be an array sensor with rectangular pixel elements having dimensions appropriate to detect light dispersed by a grating (not shown) in the spectrometer. The line scan sensor can also maintain spectral resolution by covering small wavelength width with a shorter dimension of the pixel in the dispersion direction; and collecting more light and improves in signal intensity by covering the lined up image of the fiber ends with longer dimension of the pixel. The line scan sensor may be, for example, 1024 pixels long and a single pixel wide, 2 pixels wide, 5 pixels wide, or more, as long as the line scan sensor is rectangular and has more pixels lined up in the long dispersion direction of the grating.

According to certain exemplary embodiments of the present disclosure, the exemplary SEE probe can facilitate a view in a forward direction with an increased field-of-view angle, which can add an additional value to various endoscopy systems. For example, the SEE probe according to the various exemplary embodiments of the present disclosure can be useful in in-vivo applications. The exemplary probe(s) can be configured for use in in-vivo, and, with a small size thereof, provide advantages over other large conventional probes that can require a more complex and invasive procedures for obtaining image data.

According to the various embodiments described herein, the endoscopic uses low NA fiber and changes the distribution of collection efficiency within the field to decrease collection at the center of the field and increase the collection efficiency at the periphery of the field of view. By the use of multiple layers of fibers with different tilt angles or opposite tilt angles, efficiency distribution can be further optimized and, if desired, even adjusted dynamically. The disclosed configuration of fibers may also be used on conventional endoscopes for the purpose of changing illumination distribution. It enables the use of fibers having small NA for illuminating a field of view having a larger NA than that of the fiber NA.

The novel arrangement of multiple fibers arranged around the distal end of the inner sheath enables the effective NA of the multiple fibers to be larger and cover larger image field than in conventional arrangements (e.g., fibers parallel to central fiber). The use of multiple layers of detection fibers enables uniformity of detection around different field angles. The fabrication method of tilting and attaching the fibers to the central lumen, and then polishing them all together makes it easier to polish and align all the fibers flush with the distal end of the central core (fiber and inner sheath).

Certain aspects of the various embodiment(s) of the present invention can be realized by one or more computers that reads out and executes computer executable instructions (e.g., one or more programs) recorded on a transitory or non-transitory storage medium to perform the functions of one or more of the above-described embodiment(s) and/or that includes one or more circuits for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

For example, in FIG. 12, the computer 1250 may include central processing unit (CPU) 1251, a storage memory (RAM) 1252, a user input/output (I/O) interface 1253, and a system interface 1254, which are interconnected by a system bus 1255. The computer 1250 illustrated in FIG. 12 can issue a command that can be transmitted to the imaging system via the system interface 1254. A touch panel screen can be included as part of the user interface unit 1253, in addition a key board, mouse, joy-stick, ball controller, and foot pedal can also be included as part of the user interface. The user can cause a command to be initiated to observe inside a lumen of a human body through the exemplary front-viewing SEE probe using the user interface unit/ imaging processor. For example, when the user inputs a command via the user interface 11253, the command is transmitted to the CPU 1251 for execution thereby causing the CPU to issue a command via the system interface 1254 to one or more of the light source 1202, the detector 1208, spectrometer 1206, or the FORJ 1204. The CPU 1251 is comprised of one or more processors (microprocessors) configured to read and perform computer-executable instructions stored in the storage memory 1252.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error. The term "substantially", as used herein means that, within fabrication parameters and/or measurement error.

The terms first, second, third, etc. may be used herein to describe various elements, components, regions, parts and/ or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

The foregoing merely illustrates the principles of the disclosure. Various modifications and alterations to the described exemplary embodiments will be apparent to those skilled in the art in view of the teachings herein. Indeed, the arrangements, systems and methods according to the exemplary embodiments of the present disclosure can be used with any SEE system or other imaging systems.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

LIST OF EXEMPLARY REFERENCES

The following non-patent literature (NPL) and patent publications, which are considered "nonessential material", are hereby incorporated by reference herein in their entirety:

Non-patent documents: C. Pitris et al., "A GRISM-based probe for spectrally encoded confocal microscopy", Optics Express, vol. 11, No. 2, pp. 120-124; Jan. 27, 2003. D. Yelin et al., "Three-dimensional miniature endoscopy", Nature Vol. 443 (7113), 765 (2006). G. Tearney et al., in "Spectrally encoded miniature endoscopy", Opt. Lett., 27(6): p. 412-414, 2002.

U.S. Pat. No. 8,145,018, patent application publication US 2017/0100024, U.S. Pat. No. 5,730,702, international patent application publication WO/2017/139657, U.S. Pat. No. 4,736,734.

What is claimed is:

1. An endoscopic probe extending from a proximal end to a distal end thereof, and configured to observe a sample, the probe comprising:
   a first waveguide enclosed within an inner sheath and extending from the proximal end to the distal end along an axis of the inner sheath;
   a plurality of second waveguides having at least the distal ends thereof arranged in a first ring pattern around the inner sheath to surround the distal end of the first waveguide,
   wherein, at the distal end of the inner sheath, the axis of each of the second waveguides is tilted with respect to the axis of the first waveguide by a predetermined angle,
   wherein the axis of each of the second waveguides is tilted with respect to the axis of the inner sheath,
   wherein one or more of the second waveguides has its distal end polished perpendicular to the axis of the inner sheath, and
   wherein the axis of a cone of acceptance for each of the second waveguides is tilted with respect to the axis of the first waveguide by an angle larger than the predetermined angle.

2. The probe of claim 1, wherein the distal end of each of the second waveguides is tilted with respect to the axis of the inner sheath.

3. The probe of claim 1,
   wherein the plurality of second waveguides is a plurality of optical fibers, and
   wherein one or more of the second waveguides has its distal end polished perpendicular to its fiber axis.

4. The probe of claim 1,
   wherein, at the distal end of the inner sheath, the distal ends of the plurality of second waveguides are arranged symmetrically in the first ring pattern around the inner sheath to surround the distal end of the first waveguide.

5. The probe of claim 1, further comprising:
   a locking mechanism having a plurality of openings, each opening configured to fit therein one or more of the plurality of second waveguides,
   wherein the locking mechanism is configured to lock the plurality of second waveguides with a predetermined tilt configuration around the distal end of the inner sheath.

6. The probe of claim 1, further comprising:
   an angle adjusting mechanism having a plurality of openings, each opening configured to loosely fit therein one or more of the plurality of second waveguides;
   wherein the angle adjusting mechanism is configured to adjust, at the distal end of the inner sheath, a tilt angle between the axis of each of the second waveguides with respect to the axis of the first waveguide.

7. The probe of claim 6, further comprising:
   an outer sheath extending from the proximal end to the distal end; and
   the angle adjusting mechanism arranged concentric with the inner sheath and the outer sheath,
   wherein the angle adjusting mechanism is attached at the distal end of either the inner sheath or outer sheath, and the distal ends of the second waveguides are arranged to surround the distal end of either the inner sheath or the outer sheath, and
   wherein the adjusting mechanism adjusts the tilt angle, by rotating one of the outer sheath and the inner sheath with respect to the other.

8. The probe of claim 6, further comprising:
   an outer sheath extending from the proximal end to the distal end; and
   a middle rotatable tube arranged concentric with the inner sheath and the outer sheath,
   wherein the angle adjusting mechanism is formed at the proximal end of the middle rotatable tube along an outer surface thereof, and a locking mechanism having a plurality of openings configured to fit in each opening one or more of the plurality of second waveguides is formed at the distal end of the outer sheath in the inner surface thereof, and
   wherein the angle adjusting mechanism adjusts the tilt angle by rotating the middle rotatable tube with respect to either one of the inner sheath and the outer sheath to which waveguides are attached at a portion proximal to the locking mechanism.

9. The probe of claim 1, further comprising:
a plurality of third waveguides having at least the distal ends thereof arranged in a second ring pattern around the plurality of second waveguides to surround the distal end of the first waveguide,
wherein, at the distal end of the inner sheath, the axis of each of the third waveguides is tilted with respect to the axis of the first waveguide by the predetermined angle.

10. The probe of claim 9, wherein, at the distal end of the inner sheath,
the axis of each of the second waveguides is tilted with respect to the axis of the first waveguide by the predetermined angle in a first direction, and
the axis of each of the third waveguides is tilted with respect to the axis of the first waveguide by the predetermined angle in a second direction intersecting the first direction.

11. The probe of claim 9, wherein, at the distal end of the inner sheath,
the axis of each of the second waveguides is tilted with respect to the axis of the first waveguide by the predetermined angle in a first direction, and
the axis of each of the third waveguides is tilted with respect to the axis of the first waveguide by the predetermined angle in a second direction same as the first direction.

12. The probe of claim 1, wherein the plurality of second waveguides are multi-modal (MM) optical fibers used as illumination fibers to transmit light from a light source to the sample.

13. The probe of claim 1, wherein the plurality of second waveguides are multi-modal (MM) optical fibers used as detection fibers to transmit light from the sample to a detector.

14. The probe of claim 1, wherein the plurality of second waveguides is a plurality of multi-mode (MM) optical fibers,
wherein, at the distal end of the probe, a resultant numerical aperture (NAr) of the MM optical fibers is given by NAr=sin(arcsin(NAf)+T),
where NAf is the numerical aperture of each fiber of the MM optical fibers, and T is the predetermined angle of tilt between the axis of each fiber tilted with respect to the axis of the first waveguide.

15. The probe of claim 1,
wherein one or more of the following conditions is satisfied:

0<*T*<22 degrees, 0.25<*NAr*<0.82, where T is the predetermined angle of tilt between the axis of each of the second waveguides with respect to the axis of the first waveguide, where NAr is a resultant numerical aperture (NAr) at the distal end of the probe, resulting from the plurality second waveguides, and
where NAr=sin(arcsin(NAf)+T) and NAf is the numerical aperture of each of the second waveguides.

16. The probe of claim 1, wherein the second waveguides are optical fibers wrapped around the inner sheath in a helical manner such that, at the distal end of the inner sheath, the axis of each fiber is tilted in a plane which is substantially tangent to the outer surface of the inner sheath.

17. The probe of claim 1, wherein the second waveguides are optical fibers arranged on the outer surface of the inner sheath, and wherein the distal ends of the optical fibers are tilted with respect to the axis of the inner sheath in a manner such that, at the distal end of the inner sheath, the axis of each fiber is substantially tangent to the distal edge of the inner sheath, in the plane perpendicular to the axis of inner sheath.

18. The probe of claim 1, further comprising:
a plurality of third waveguides having at least the distal ends thereof arranged in a second ring pattern around the inner sheath to surround the distal end of the first waveguide, the second ring pattern being concentric to first ring pattern,
wherein, at the distal end of the inner sheath, the axis of each of the second waveguides is tilted with respect to the axis of the first waveguide by a first tilt angle T1, and the axis of each of the third waveguides is tilted with respect to the axis of the first waveguide by a second tilt angle T2, where T2 >T1.

19. An endoscopic system comprising:
a processor,
a first waveguide enclosed within an inner sheath and extending from the proximal end to the distal end along an axis of the inner sheath, the first waveguide configured to irradiate a sample with light from a light source;
a plurality of second waveguides having at least the distal ends thereof arranged in one or more ring patterns around the inner sheath to concentrically surround the distal end of the first waveguide,
wherein, at the distal end of the inner sheath, the axis of each of the second waveguides is tilted with respect to the axis of the first waveguide by a tilt angle T where 0<T≤22 degrees,
wherein the plurality of second waveguides are configured to collect light from the sample and deliver the collected light to a detector or an spectrometer; and
wherein the processor is configured to process data from the spectrometer or detector and form an image.

* * * * *